United States Patent [19]

Ito et al.

[11] Patent Number: 4,839,373
[45] Date of Patent: Jun. 13, 1989

[54] QUATERNARY AMMONIUM AND BENZOTHIAZOLE MICROBICIDAL PRESERVATIVE COMPOSITION

[75] Inventors: Yosuke Ito, Otsu; Yasuhiro Nomura, Takatsuki; Sakae Katayama, Osaka, all of Japan

[73] Assignee: Buckman Laboratories International, Inc., Memphis, Tenn.

[21] Appl. No.: 103,819

[22] Filed: Oct. 2, 1987

[30] Foreign Application Priority Data

May 28, 1987 [JP] Japan ................................ 62-132871

[51] Int. Cl.$^4$ ............................................ A01N 43/78
[52] U.S. Cl. .................................................... 514/367
[58] Field of Search ......................... 514/642, 643, 367

[56] References Cited

U.S. PATENT DOCUMENTS

| | | | |
|---|---|---|---|
| 4,125,628 | 11/1978 | Goldhaft et al. | 514/642 |
| 4,285,765 | 8/1981 | Pera et al. | 514/367 |
| 4,479,961 | 10/1984 | Martin | 514/367 |

*Primary Examiner*—Paul Lieberman
*Assistant Examiner*—Christine A. Skane
*Attorney, Agent, or Firm*—Finnegan, Henderson, Farabow, Garrett & Dunner

[57] ABSTRACT

A composition comprising a quaternary ammonium compound and 2-(thiocyanomethylthio)benzothiazole. The composition can be useful as a microbicide and preservative for preventing the deterioration of various types of industrial raw materials and products by inhibiting the growth of microorganisms.

30 Claims, 2 Drawing Sheets

QUATERNARY AMMONIUM AND BENZOTHIAZOLE MICROBICIDAL PRESERVATIVE COMPOSITION

FIELD OF THE INVENTION

The present invention relates generally to a composition and more particularly, to a microbicidal preservative composition comprising a quaternary ammonium compound and 2-(thiocyanomethylthio)benzothiazole (hereafter TCMTB).

BACKGROUND OF THE INVENTION

Various chemicals such as organomercury compounds, organotin compounds and chlorinated phenols have been used as industrial preservative fungicides. However, the toxicity of these compounds and environmental contamination caused by these compounds are known problems.

The quaternary ammonium compounds and TCMTB used in the present invention are known individually as low toxicity antimicrobials. However, these compounds each possess a narrow antibacterial spectrum and, when used alone, have limited ability to completely prevent the growth of microorganisms. Thus, it was not possible to effectively prevent the development of microorganisms.

SUMMARY OF THE INVENTION

The present invention can overcome the problems and disadvantages of the prior art by providing a composition comprising a quaternary ammonium compound and TCMTB which has improved microbicidal and preservative effects at lower concentrations than the prior art, has low toxicity and is effective against a wider spectrum of microorganisms. The instant inventors discovered that the combined use of a quaternary ammonium compound and 2-(thiocyanomethylthio)-benzothiazole achieve superior microbicidal preservative activity at low concentrations against a wide range of microorganisms.

The present invention also provides a method for inhibiting the growth of a microorganism which comprises the step of contacting the microorganism with the composition of the invention in an amount synergistically effective to inhibit the growth of the microorganism. The invention also provides a method of preventing decay or deterioration of a material capable of supporting growth of a microorganism comprising the step of contacting the material with the composition of the invention in an amount synergistically effective to prevent the decay or deterioration of the material. The effective amount varies in accordance with the material or product to be treated and can readily be determined, without undue experimentation, by one skilled in the art.

The microbicidal preservative composition of the invention is useful in preventing the deterioration of various types of industrial raw materials and products such as dyes, glues, lumber, leather, textiles and pulp by microorganisms such as bacteria, mold and fungi.

Additional advantages of the invention will be set forth in part in the description which follows, and in part will be obvious from the description, or may be learned by practice of the invention. The objects and advantages of the invention may be realized and obtained by means of instrumentalities and combinations particularly pointed out in the appended claims.

The present invention provides a composition comprising a quaternary ammonium compound (hereinafter "QAC") and TCMTB. The QAC is represented by the formula (I):

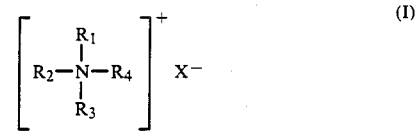

wherein $R_1$ is an alkyl group having from 8 to 18 carbon atoms, or an alkenyl group having from 8 to 18 carbon atoms, $R_2$ is a alkyl group having from 1 to 5 carbon atoms, an alkyl group having from 8 to 18 carbon atoms or an alkenyl group having from 8 to 18 carbon atoms or an aralkyl group; $R_3$ and $R_4$ are independently alkyl groups having from 1 to 5 carbon atoms; and X is a halogen atom.

BRIEF DESCRIPTION OF THE DRAWINGS

The accompanying drawings, which are incorporated in and constitute a part of this specification, illustrate several exemplary embodiments of the invention and together with the description, serve to explain the principles of the invention.

Figure 1:
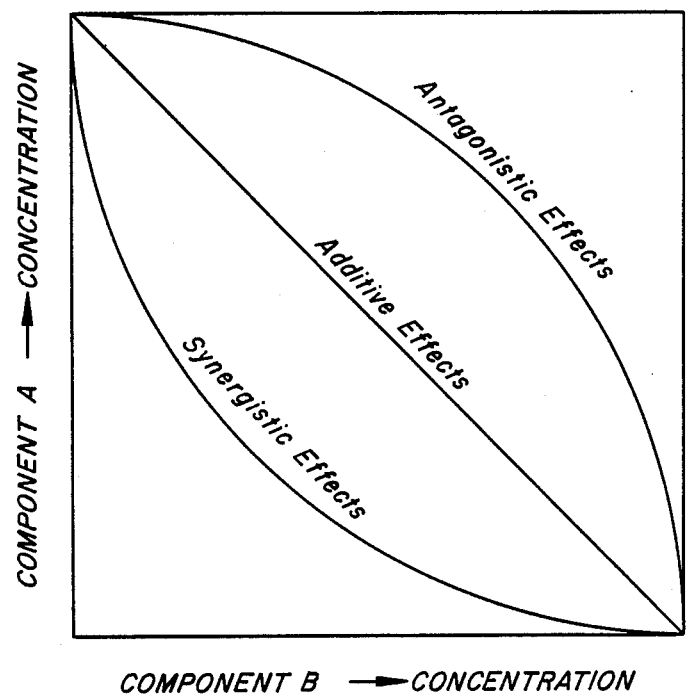
FIG. 1 is a graph showing the evaluation standards of the synergistic effects of the composition of the invention against microorganisms by the TDMIC curve in the binary dilution method.

The foregoing and other features and advantages of the present invention will be made more apparent from the following description of the preferred embodiments.

DETAILED DESCRIPTION OF THE PREFERRED EMBODIMENTS

Reference will now be made in detail to the preferred embodiments of the invention.

In accordance with the invention, the present invention can provide a low toxicity microbicidal preservative composition comprising a QAC of the formula (I):

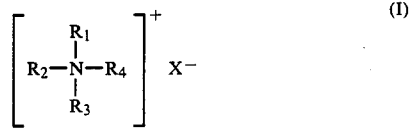

wherein $R_1$, $R_2$, $R_3$ and $R_4$ are defined as set forth above, and TCMTB. The combination of QAC and TCMTB is employed in an amount effective to synergistically inhibit the growth of a microorganism and prevent the decay or deterioration of the material or product to which the composition is applied. When $R_2$ is an aralkyl group, it is preferably a benzyl or phenethyl group. X may be chlorine, bromine, iodine, etc. but is preferably chlorine.

The weight ratio of the QAC:TCMTB is from 30:1 to 1:10, preferably from 20:1 to 1:10, and more preferably from 10:1 to 1:2, although the ratio varies depending upon the intended use, and the microorganism, material or product to which it is applied.

The microbicidal preservative composition of the invention which combines the QAC and TCMTB can demonstrate an unexpected synergistic antimicrobial effect between the respective components and achieves superior, i.e. greater than additive, microbicidal preservative activity at low concentrations against a wide range of microorganisms.

Preferably, the QAC is an alkyl $C_8$–$C_{18}$ trimethylammonium halide such as octyltrimethylammonium chloride, decyltrimethylammonium chloride, dodecyltrimethylammonium chloride, hexadecyltrimethylammonium chloride, stearyltrimethylammonium chloride, a dialkyl $C_8$–$C_{18}$ dimethylammonium halide such as dioctyldecyldimethylammonium chloride, dioctyldimethylammonium chloride, didecyldimethylammonium chloride, dioctyldodecyldimethylammonium chloride, dihexadecyldimethylammonium chloride, dioctadecyldimethylammonium chloride, an alkyl $C_8$–$C_{18}$ benzyldimethylammonium halide such as dodecyldimethylbenzylammonium chloride, hexadecyldimethylbenzylammonium chloride, octadecyldimethylbenzylammonium chloride. The QAC may be used in mixtures, particularly mixtures having mixed alkyl groups derived from common fats and oils such as $C_8$–$C_{18}$ alkyltrimethylammonium chloride, $C_8$–$C_{18}$ dialkyldimethylammonium chloride, and $C_8$–$C_{18}$ alkyldimethylbenzylammonium chloride. Preferably, dioctyldimethylammomium chloride, didecyldimethylammonium chloride, dodecyldimethylbenzylammonium chloride, hexadecyldimethylbenzylammonium chloride or octadecyltrimethylammonium chloride is employed.

Depending upon the specific application, the composition of the present invention may be prepared in various forms. It may be prepared in liquid form in which it is useful to prevent the decay and molding of starch paste solution, wet pulp and lumber. The composition may be dissolved in solvents such as for example, N,N-dimethylformamide, monochlorobenzene, cyclohexanone, tetrahydrofuran, diethylene glycol monomethyl ether and ethylene glycol monophenyl ether. An emulsion can be prepared by adding a surfactant, if necessary, and emulsifying in water. Preferably, nonionic surfactants are employed such as polyoxyethylene alkylphenol ether, polyoxyethylene-polyoxypropylene block copolymer, polyoxyethylene alkyl ether and polyoxyethylene fatty acid ester. The composition of the present invention can also be used as a powder when the subject to be treated is a powder, in which case the composition is preferably deposited on a carrier such as diatomaceous earth or kaolin. The composition can also be prepared in paste form by dissolving it in an organic solvent and adding a surfactant. The paste can be applied to lumber for microbicidal and preservative treatment. Other microbicidal preservatives such as dithiocyanomethane and 2-(4-thiazolyl)-1H-benzimidazole, or other chemicals, such as insecticides, can be added to the present composition.

The concentrations of the components of the composition of the present invention vary depending on the intended use and the microorganism, material or product to which it is applied. For example, from 5 to 100 mg/kg of QAC and from 1 to 100 mg/kg of TCMTB can be added to prevent decay of glues such as starch paste and to prevent molding of wet pulp. In lumber, from 0.1 to 10 g/m² of QAC and from 0.5 to 1 g/m² of TCMTB should be absorbed when the intent is to prevent molding, and from 1 to 10 g/m² of QAC and from 0.2 to 5 g/m² of TCMTB should be applied when the intent is to prevent decay.

The invention will be further clarified by the following examples, which are intended to be merely illustrative of the invention.

EXAMPLE 1

Synergistic Effect of the Combined Use of QAC and TCMTB Against Microorganisms

The synergistic effects of the combined use of QAC and TCMTB against microorganisms were measured by the binary dilution method. The two components were diluted to specific concentrations and then added to culture medium. The medium was then inoculated with microorganisms and cultured under designated conditions. The concentrations at which no growth of microorganisms was found were taken as the minimal inhibitory concentrations by the binary dilution method.

FIG. 1 is a graph of the minimal inhibitory concentrations of each component (TCMTB: Component A, QAC: Component B) using common scale coordinates. The curve of this graph, i.e. the region above the TDMIC curve, shows the proliferation inhibition region. The area below the TDMIC curve shows the proliferation region. Agreement of the diagonal and TDMIC curve shows additive effects. The fact that the curve is lower than the diagonal demonstrates synergistic effects.

EXAMPLE 2

Synergistic Effect of the Combined Use of QAC and TCMTB Against Bacteria

The synergistic effects of the combined use of QAC and TCMTB were evaluated against *Bacillus subtilis* of the genus Bacillus, a bacteria detected frequently in decayed latex, starch paste, starch slurry and coating color.

Bouillon medium was used as the medium. It was inoculated with a set quantity of a bacterial solution that had been precultured overnight. After shake culturing for 24 hours at 37° C., the concentration at which the medium was not turbid was determined.

Didecyldimethylammonium chloride (hereafter "DDAC") was used as the QAC.

Figure 2:
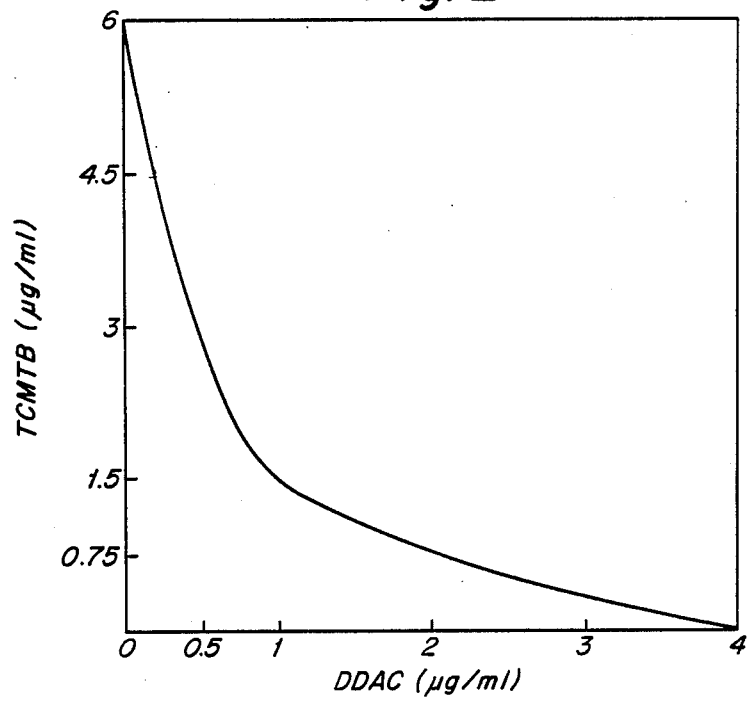
FIG. 2 sets forth the TDMIC curve of the composition of the invention against Bacillus subtilis.

The results are set forth in FIG. 2.

As shown in FIG. 2, the TDMIC curve against Bacillus subtilis demonstrates clear synergistic effects. The concentrations at which the combination of DDAC and TCMTB completely inhibited bacterial growth were 1 μg/ml and 1.5 μg/ml respectively. Since bacterial growth was inhibited individually by 6 μg/ml of TCMTB and 4 μg/ml of DDAC, the composition of the present invention manifested marked synergistic effects because it was capable of suppression at ¼ the sum of the quantities used alone. Examples of other concentration combinations that demonstrated synergistic effects are set forth in Table 1.

TABLE 1

| TCMTB (μg/ml) | DDAC (μg/ml) |
| --- | --- |
| 4.5 | 0.5 |
| 3.0 | 0.5 |
| 3.0 | 1.0 |
| 1.5 | 2.0 |
| 0.75 | 2.0 |

TABLE 1-continued

| TCMTB (μg/ml) | DDAC (μg/ml) |
| --- | --- |
| 0.75 | 3.0 |

EXAMPLE 3

Synergistic Effects of the Combined Use of TCMTB and QAC Against Molds

The synergistic effects of the combined use of TCMTB and QAC were evaluated against *Aspergillus niger* of the species Asperqillus, a mold that develops frequently in wet pulp, starch paste and coating color.

Czapek medium was used as the medium. Spores were collected from a previous slant cultured stock strain. The medium was inoculated with a set amount of a solution of spores suspended in sterilized water. After shake culturing for 72 hours at 27° C., the concentration at which no mycelia developed in the medium was determined. The results are set forth in FIG. 3.

Figure 3:
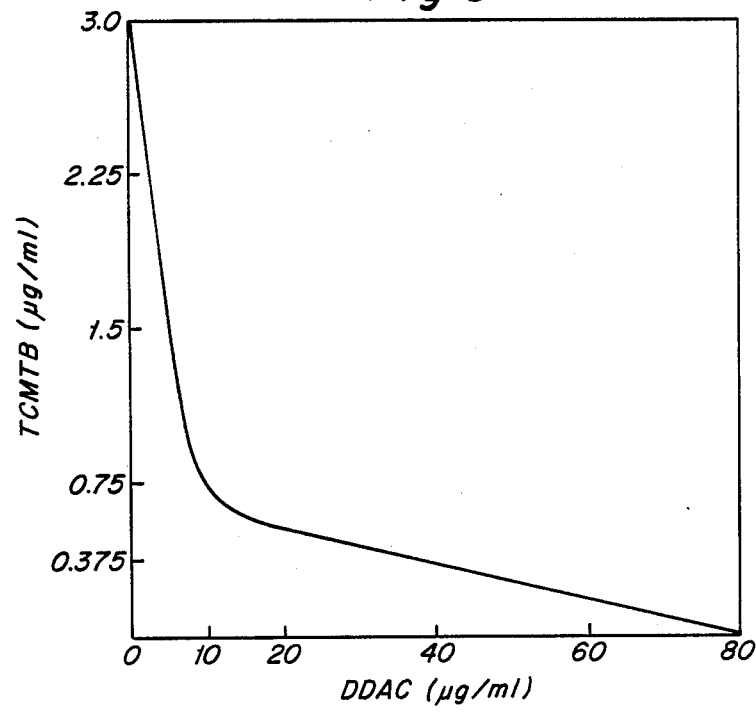
FIG. 3 sets forth the TDMIC curves of the composition of the invention against Aspergillus niger.

As shown in FIG. 3, the TDMIC curve against *Asperqillus niger* demonstrated clear synergistic effects. The synergistic effects of the combination of the two components that completely inhibited growth of the organisms appeared at, for example, a TCMTB concentration of 0.75 μg/ml and a DDAC concentration of 10 μg/ml. Since growth of the organisms was inhibited individually by 3.0 μg/ml of TCMTB and 80 μg/ml of DDAC, the composition of the present invention permitted inhibition at ¼ and ⅛ the quantities of the individual components when used alone, demonstrating strong synergistic effects. Examples of concentration combinations of TCMTB and DDAC that demonstrate synergistic effects are given in Table 2.

TABLE 2

| TCMTB (μg/ml) | DDAC (μg/ml) |
| --- | --- |
| 2.25 | 10 |
| 1.5 | 10 |
| 1.5 | 20 |
| 0.75 | 20 |
| 0.75 | 40 |
| 0.375 | 40 |
| 0.375 | 60 |

EXAMPLE 4

Preservative Effect of the Composition of the Invention In Starch Paste Solution Cornstarch was dispersed in water in a weight ratio of 5%, and paste solution was prepared by heating to 90-95° C. while stirring. After cooling, 1% already decayed paste solution was added and 100 g portions were poured into 140 ml glass bottles. DDAC, TCMTB and a mixture of DDAC:TCMTB=1:1 were dissolved in N,N-dimethylformamide and added to make the concentrations set forth in Table 3. Culture was conducted at 37° C. and the bacterial counts were measured over time. The results are set forth in Table 3.

TABLE 3

| Chemical Name | Blank | DDAC | TCMTB | 1:1 Mixture |
| --- | --- | --- | --- | --- |
| Added Concentration | 0 μg/ml | 15 μg/ml | 15 μg/ml | 30 μg/ml |
| Days Elapsed | | | | |
| 0 | $1.9 \times 10^4$ | — | — | — |
| 2 | $7.9 \times 10^5$ | $<10^2$ | $8.8 \times 10^3$ | $<10^2$ |
| 4 | $7.7 \times 10^6$ | $<10^2$ | $9.3 \times 10^4$ | $<10^2$ |
| 6 | $3.8 \times 10^7$ | $5 \times 10^2$ | $8.6 \times 10^5$ | $<10^2$ |
| 8 | $6.9 \times 10^7$ | $2.0 \times 10^3$ | $1.4 \times 10^6$ | $<10^2$ |
| 10 | $7.6 \times 10^7$ | $5.9 \times 10^4$ | $4.3 \times 10^6$ | $<10^2$ |

The figures in the table represent the live bacterial counts (cells/ml). As shown in Table 3, the DDAC:TCMTB=1:1 mixture demonstrated clearly superior preservative activity in comparison to the same concentrations of the chemicals alone. Synergistic effects demonstrating enhanced preservative activity were thus obtained.

EXAMPLE 5

Microbicidal Activity of the Composition of the Invention In Wet Pulp

Test sheets were produced by punching wet pulp (LBKP) into 5 cm diameter pieces. DDAC, TCMTB and DDAC:TCMTB=10:1 mixture were dissolved in N,N-dimethylformamide and applied uniformly by pipette to prepare the concentrations set forth in Table 4 in relation to the dry weight of the pulp. 0.1 ml of the various concentrations were applied to the test sheets. Sheets containing 0.1 ml of N,N-dimethylformamide were used as the controls. The test sheets were placed in petri dishes 9 cm in diameter into which culture medium of the following composition had previously been poured and solidified.

To 1 liter of deionized water, 3.0 g $NH_4NO_3$, 1.0 g $KH_2PO_4$, 0.5 g $MgSO_4.7H_2O$, 0.25 g KCl, pb 0.222 g $FeSO_4$ and 25 g agar were added. Spores of the genus Aspergillus, Penicillium and Trichoderma that appear frequently in wet pulp, and are among the molds separated and stored from wet pulp, were suspended in sterilized water and the designated quantities were uniformly applied on top of the aforementioned sheets. Culture was conducted at 27° C. and the growth of the molds was observed visually over time. The results are shown in Table 4.

TABLE 4

| Chemical Name | Subject | DDAC | TCMTB | 10:1 Mixture |
| --- | --- | --- | --- | --- |
| Added Concentration | 0 mg/kg | 20 mg/kg | 2 mg/kg | 22 mg/kg |
| Days Elapsed | | | | |
| 5 | + | — | — | — |
| 10 | ++ | + | — | — |
| 15 | +++ | + | — | — |
| 20 | +++ | ++ | + | — |
| 25 | +++ | ++ | + | — |
| 30 | +++ | ++ | ++ | — |

The evaluation standards in Table 4 are as follows:
—: No growth of mold found on the sheets
+: Growth of mold found on less than ⅓ of the sheet
++: Growth of mold found on from ⅓ to ⅔ of the sheet
+++: Growth of mold found on ⅔ or more of the sheet As shown in Table 4, mold development was completely inhibited by addition of 22 mg/kg of the DDAC:TCMTB=10:1 mixture. The microbicidal activity was clearly superior to that obtained by the same concentration of the chemicals alone and synergistic effects were thus obtained.

EXAMPLE 6

Microbicidal Activity of the Composition of the Invention Against Fungi in Wood A microbicidal test using DDAC and TCMTB alone and a mixture of DDAC:TCMTB=10:3 was conducted against molds that frequently grow in wood. The test method was in accordance with regulation No. 2 "Fungicidal test methods of fungicides for wood" of the Japan Wood Preservation Association (abbreviated JWPA). The concentrations shown in Table 5 were tested.

The chemicals tested are shown in Table 5. The numbers in the table represent the respective parts by weight of each component.

TABLE 5

|  | Preparation 1 | Preparation 2 | Preparation 3 |
|---|---|---|---|
| DDAC | 10 | — | 10 |
| TCMTB | — | 3 | 3 |
| Ethanol | 2 | — | 2 |
| Diethylene glycol monomethyl ether | — | — | 50 |
| Diethylene glycol | — | 92 | 27 |
| Nonylphenol ethylene oxide adduct | — | 5 | — |
| Tap Water | 88 | — | 8 |

The molds tested were:
$A_1$: *Aspergillus niger*
$A_2$: *Penicillium funiculosum*
$A_3$: *Aureobasidium pullulans*
$A_4$: *Gliocladium riruns*
$A_5$: *Rhizopus javanicus*

The test sheets were prepared as follows. Rectangular sheets of Japanese beech (20×3×50 mm) were immersed for 3 minutes in solutions of Preparations 1, 2 and 3 diluted to 2.0%, 4.0% and 6.0% by weight by tap water. These were subsequently dried for 2 days and taken as treated test pieces.

2% agar solution steam sterilized under high pressure was poured and solidified in sterilized petri dishes (90 mm in diameter). A polypropylene mesh was placed on top of the agar as a stand so that the test pieces and agar would not come into direct contact. Three test pieces were placed on the stand and spore suspensions of the various test molds were poured on top. Six treated pieces (2 per petri dish) were used for each concentration. Culture was conducted for 4 weeks at 26° C. The effects were evaluated by examining the mold development in each individual test sheet after 4 weeks for each type of mold and each concentration. The evaluation values were determined according to the following standards.

| Evaluation Value | Mold Growth |
|---|---|
| 0 | Absolutely no mold growth found on test sheet |
| 1 | Mold growth found on only sides of test sheet |
| 2 | Mold growth found on less than ⅓ of the surface area of the test sheet |
| 3 | Mold growth found on more than ⅓ of the surface area of the test sheet |

The damage values (D) in Table 6 were determined by the following equation after determining the total mean evaluation value (S) for each concentration.

Total mean evaluation value $(S) = A_1 + A_2 + A_3 + A_4 + A_5$ ($A_1, A_2 \ldots A_5$: Mean evaluation value of each mold species)

$$D = \frac{S}{S_0} \times 100$$

$S_0$: Total mean evaluation value of untreated test sheet
$S$: Total mean evaluation value of treated test sheet of a certain concentration The results are shown in Table 6.

TABLE 6

| Chemical | Treatment Concentration % by weight | Amount Absorbed (g/m²) | Mean Evaluation Value of Each Organism | | | | | S | D |
|---|---|---|---|---|---|---|---|---|---|
| | | | $A_1$ | $A_2$ | $A_3$ | $A_4$ | $A_5$ | | |
| Preparation 1 | 6.0 | 6.2 | 2.2 | 2.2 | 0 | 1.5 | 1.0 | 6.9 | 46 |
| | 4.0 | 4.1 | 2.4 | 2.4 | 0.7 | 1.8 | 2.2 | 9.5 | 63 |
| | 2.0 | 2.0 | 3 | 2.4 | 1.3 | 3 | 3 | 12.7 | 85 |
| Preparation 2 | 6.0 | 6.1 | 1.0 | 0 | 0 | 2.3 | 0 | 3.3 | 22 |
| | 4.0 | 4.0 | 2.4 | 0.7 | 0 | 3 | 2.4 | 8.5 | 57 |
| | 2.0 | 2.0 | 3 | 2.4 | 0.7 | 3 | 3 | 12.1 | 81 |
| Preparation 3 | 6.0 | 6.2 | 0 | 0 | 0 | 0 | 0 | 0 | 0 |
| | 4.0 | 4.1 | 1.0 | 0 | 0 | 0 | 0 | 1.0 | 7 |
| | 2.0 | 2.0 | 1.0 | 0 | 0 | 1.0 | 0 | 2.0 | 13 |

The damage value (D) at which essential microbicidal effects can be expected is not more than 30. According to Table 5, Preparation 1 exceeds 30 even in a treatment concentration of 6.05 (amount absorbed 6.2 g/m²). Preparation 2 also exceeds 30 in a treatment concentration of 4.0% (amount absorbed 4.0 g/m²). In contrast to this, Preparation 3, in accord with the present invention, is below 30 even in a treatment concentration of 2.0% (amount absorbed 2.0 g/m²). Together with demonstrating superior microbicidal effects, this evidences synergistic effects.

The most effective microbicidal activity resulted from the use of Preparation 3 in which the active ingredients are DDAC and TCMTB. Preparation 3 demonstrated superior microbicidal activity even in a low concentration even against $A_1$, $A_4$ and $A_5$ molds against which Preparation 1 (active ingredient DDAC) and Preparation 2 (active ingredient TCMTB) have little microbicidal activity.

Considering that the microbicidal activity against $A_4$ molds was unsatisfactory even by individual or combined use (not shown in Table 6) of MBTC (methylene bisthiocyanate) and TCMTB, which are representative of commercial fungicides, the effects of the present invention are even more remarkable than anticipated.

EXAMPLE 7

Preservative Activity of the Composition of the Invention Against Microorganisms in Wood A preservative activity test was conducted against various types of organisms that rot wood using DDAC and TCMTB alone and the two in combination. Preparations 1–3 set forth above in Example 6 were utilized. The test method was according to regulation No. 1 "Wood preservative activity test method" of the JWPA.

The same chemicals as in Example 5 were tested.
The test organisms employed were:

(I) Oouzuratake: *Tyromyces palustris*
(II) Kawaratake: *Coriolus versicolor*
(III) Namidatake: *Serpula lacrymans*

The test sheets were prepared as follows. Rectangular sheets of Japanese cedar, red pine and beech (5×20×40 mm, flat surfaced, known holes sealed with normal temperature curing epoxy type resin) were used as the test sheets. The chemicals of Preparations 1, 2 and 3 were diluted to 15, 20 and 25% by weight by tap water and uniformly applied by brush to the aforementioned test pieces to make a proportion of 110±10 g/m². After drying, the pieces were divided into two groups, one submitted to a weathering test and one not. The former were treated according to the JWPA weathering procedure method. All of the test sheets were then dried until reaching a constant weight at 60° C. and taken as treated test sheets.

In the preservative activity test, JIS modified medium (peptone=0.5%, malt extract=1%, glucose=2.5%, $KH_2PO_4$=0.3%, $MgSO_4 \cdot 7H_2O$=0.2%) was used as the culture medium. Culture was conducted by combining the test sheets of the three types of wood and the wood rotting organisms as shown in the following table.

| Type of Wood | Organism | Culture Temperature (°C.) |
|---|---|---|
| Japanese Cedar | *Tyromyces palustris* | 26 ± 2 |
| Japanese beech | *Coriolus versicolor* | 26 ± 2 |
| Red Pine | *Serpula lacrymans* | 20 ± 2 |

After culturing for 56 days, the organisms adhering to the test pieces were removed and the pieces were dried to a constant weight at 60° C. The percentage weight loss was determined and the preservative activity value was calculated by the following equation.

$$D = \frac{S_0 - S}{S_0} \times 100$$

wherein D represents the preservative activity value; $S_0$ represents the mean weight loss percentage of untreated test sheet and S represents the mean weight loss percentage of chemical treated test sheet. The test results are shown in Table 7.

isms were more than 25% by weight for both Preparations 1 and 2, while that of Preparation 3 was from 20 to 25% by weight. Together with demonstrating the superior preservative activity, marked synergistic effects were found.

Superior microbicidal preservative effects were manifested by the synergistic antimicrobial and preservative activity of the ingredients of the composition of the present invention. This makes it possible to effectively prevent microbial damage at lower cost. The preparation of the present invention is also advantageous in terms of environmental contamination because both the QAC and TCMTB are of low toxicity.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:
1. A composition comprising
(a) a quaternary ammonium compound of the formula (I):

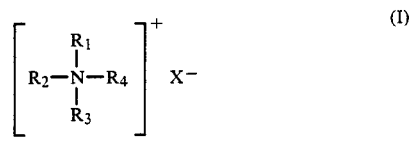

wherein
$R_1$ is selected from the group consisting of an alkyl group having from 8 to 18 carbon atoms and an alkenyl group having from 8 to 18 carbon atoms;
$R_2$ is selected from the group consisting of an alkyl group having from 1 to 5 carbon atoms, an alkyl group having from 8 to 18 carbon atoms, an alkenyl group having from 8 to 18 carbon atoms and an aralkyl group;
$R_3$ and $R_4$ are independently alkyl groups having from 1 to 5 carbon atoms; and
X is a halogen atom;
and (b) 2-(thiocyanomethylthio)benzothiazole, wherein the weight ratio of the quaternary ammonium compound of the formula (I) to the 2-(thiocyanomethylthio)benzothiazole ranges from 30:1 to 1:10.

TABLE 7

| Treatment Chemical | | *Coriolus versicolor*- Japanese beech | | *Tyromyces palustris*- Japanese cedar | | *Serpula lacrymans*- Red Pine | |
|---|---|---|---|---|---|---|---|
| Name of Chemical | Concentration % | No Weathering Procedure | With Weathering Procedure | No Weathering Procedure | With Weathering Procedure | No Weathering Procedure | With Weathering Procedure |
| Preparation 1 | 15 | 21 | 0 | 36 | 0 | 59 | 32 |
|  | 20 | 54 | 39 | 69 | 43 | 75 | 63 |
|  | 25 | 75 | 70 | 72 | 62 | 89 | 71 |
| Preparation 2 | 15 | 26 | 0 | 36 | 22 | 57 | 34 |
|  | 20 | 52 | 33 | 79 | 47 | 82 | 68 |
|  | 25 | 80 | 75 | 99 | 79 | 100 | 87 |
| Preparation 3 | 15 | 51 | 47 | 82 | 69 | 83 | 80 |
|  | 20 | 85 | 74 | 91 | 88 | 100 | 98 |
|  | 25 | 100 | 99 | 100 | 100 | 100 | 100 |
| Untreated Weight Loss Percentage (%) | | 31.4% | | 33.2% | | 27.5% | |

The preservative activity value at which essential preservative effects can be expected is at least 85. As is evident from Table 7, the effective treatment concentrations for all combinations of woods and rotting organ- 2. A composition comprising a microbicidally effective amount of a combination of
(a) a compound of the formula (I):

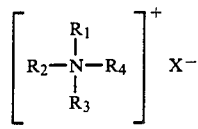 (I)

wherein
- R₁ is selected from the group consisting of an alkyl group having from 8 to 18 carbon atoms and an alkenyl group having from 8 to 18 carbon atoms;
- R₂ is selected from the group consisting of an alkyl group having from 1 to 5 carbon atoms, an alkyl group having from 8 to 18 carbon atoms, an alkenyl group having from 8 to 18 carbon atoms and an aralkyl group;
- R₃ and R₄ are independently alkyl groups having from 1 to 5 carbon atoms; and
- X is a halogen atom; and (b) 2-(thiocyanomethylthio)benzothiazole.

3. The composition of claim 2 wherein R₂ is an aralkyl group.

4. The composition of claim 3 wherein the aralkyl group is selected from the group consisting of a benzyl group and a phenethyl group.

5. The composition of claim 2 wherein X is chlorine.

6. The composition of claim 2 wherein said quaternary ammonium compound is didecyldimethylammonium chloride.

7. The composition of claim 1 wherein said weight ratio ranges from 20:1 to 1:10.

8. The composition of claim 7 wherein said weight ratio ranges from 10:1 to 1:2.

9. The composition of claim 8 wherein said weight ratio is 1:1.

10. The composition of claim 2 further comprising an organic solvent.

11. The composition of claim 2 further comprising a surfactant.

12. The composition of claim 11 wherein said surfactant is nonionic.

13. The composition of claim 2 further comprising a carrier selected from the group consisting of diatomaceous earth and kaolin.

14. A method of inhibiting the growth of a microorganism comprising the step of contacting said microorganism with said composition of claim 1 in an amount synergistically effective to inhibit the growth of said microorganism.

15. The method of claim 14 wherein said microorganism is a bacteria.

16. The method of claim 15 wherein said bacteria is *Bacillus subtilis*.

17. The method of claim 14 wherein said microorganism is a mold.

18. The method of claim 17 wherein said mold is Asperqillus niqer.

19. The method of claim 14 wherein said microorganism is a fungus.

20. The method of claim 14 wherein said microorganism is selected from the group consisting of Aspergillus, Penicillium and Trichoderma.

21. The method of claim 14 wherein said microorganism is selected from the group consisting of *Aspergillus niger, Penicillium funiculosum, Aureobasidium pullulans, Gliocladium riruns* and *Rhizopus javanicus*.

22. A method of preventing decay or deterioration of a material wherein said decay or deterioration is caused by the growth of a microorganism comprising the step of contacting said material with the composition of claim 1 in an amount synergistically effective to prevent the decay or deterioration of said material.

23. The method of claim 22 wherein said material is cornstarch paste.

24. The method of claim 22 wherein said material is wood.

25. The method of claim 22 wherein said material is wet pulp.

26. The method of claim 22 wherein said microorganism is selected from the group consisting of *Tyromyces palustris, Coriolus versicolor* and *Serpula lacrymans*.

27. The method of claim 22 wherein said microorganism is selected from the group consisting of *Asperqillus niger, Penicillium funiculosum, Aureobasidium pullulans, Gliocladium riruns,* and *Rhizopus javanicus*.

28. The composition of claim 2 wherein said weight ratio ranges from 20:1 to 1:10.

29. The composition of claim 28 wherein said weight ratio ranges from 10:1 to 1:2.

30. The composition of claim 29 wherein said weight ratio is 1:1.

* * * * *

UNITED STATES PATENT AND TRADEMARK OFFICE
CERTIFICATE OF CORRECTION

PATENT NO. : 4,839,373
DATED : June 13, 1989
INVENTOR(S) : Yosuke Ito, Otsu; Yasuhiro Normura, Takatsuki; Sakae Katayama, Osaka, all of Japan It is certified that error appears in the above-identified patent and that said Letters Patent is hereby corrected as shown below:

Claim 2, column 11, line 20; before the period (.) insert the phrase --wherein the weight ratio of the quarternary ammonium compound of the formula (I) to the 2-(thiocyanomethylthio)benzothiazole ranges from 30:1 to 1:10--

Claim 18, column 12, line 11: "Asperquillus niqer" should be --Aspergillus niger--.

Claim 20, column 12, lines 15-16: "Aspergillus, Penicillium and Trichoderma" should be Aspergillus, Penicillium and Trichoderma.

Claim 27, column 12, line 37: "Asperquillus" should be --Aspergillus--.

Signed and Sealed this

Eighth Day of May, 1990

Attest:

HARRY F. MANBECK, JR.

*Attesting Officer*     *Commissioner of Patents and Trademarks*